US008251989B1

(12) United States Patent　　(10) Patent No.: US 8,251,989 B1
Newton et al.　　(45) Date of Patent: Aug. 28, 2012

(54) COMBINED BIPOLAR AND MONOPOLAR ELECTROSURGICAL INSTRUMENT AND METHOD

(75) Inventors: David Newton, Longmont, CO (US); Jerry Keane, Louisville, CO (US); Warren Taylor, Longmont, CO (US)

(73) Assignee: Encision, Inc., Boulder, CO (US)

( * ) Notice: Subject to any disclaimer, the term of this patent is extended or adjusted under 35 U.S.C. 154(b) by 1246 days.

(21) Appl. No.: 11/762,568

(22) Filed: Jun. 13, 2007

Related U.S. Application Data

(60) Provisional application No. 60/804,601, filed on Jun. 13, 2006.

(51) Int. Cl.
*A61B 18/12* (2006.01)
(52) U.S. Cl. .......................................... 606/34
(58) Field of Classification Search .............. 606/37–40, 606/34
See application file for complete search history.

(56) References Cited

U.S. PATENT DOCUMENTS

| | | |
|---|---|---|
| 984,756 A | 2/1911 | Frisch |
| 1,754,806 A | 4/1930 | Stevenson |
| 2,004,559 A | 6/1935 | Wappler et al. |
| 2,008,367 A | 7/1935 | Rhinevault |
| 2,448,741 A | 9/1948 | Scott et al. |
| 2,741,248 A | 4/1956 | Woodhall |
| 3,070,132 A | 12/1962 | Sheridan |
| 3,580,983 A | 5/1971 | Jackson |
| 3,585,985 A | 6/1971 | Gould |
| 3,601,126 A | 8/1971 | Estes |
| 3,706,008 A | 12/1972 | Kremer |
| 3,707,149 A | 12/1972 | Hao et al. |
| 3,804,096 A | 4/1974 | Gonser |
| 3,834,392 A | 9/1974 | Lampman et al. |
| 3,838,242 A | 9/1974 | Goucher |
| 3,895,635 A | 7/1975 | Justus et al. |
| 3,898,991 A | 8/1975 | Ikuno et al. |
| 3,905,373 A | 9/1975 | Gonser |
| 3,913,583 A | 10/1975 | Bross |
| 3,933,157 A | 1/1976 | Bjurwill et al. |
| 3,946,738 A | 3/1976 | Newton et al. |
| 3,963,856 A | 6/1976 | Carlson et al. |
| 3,974,833 A | 8/1976 | Durden |
| 3,994,287 A | 11/1976 | Turp et al. |
| 4,003,380 A | 1/1977 | Wien |
| 4,043,342 A | 8/1977 | Morrison |
| 4,084,594 A | 4/1978 | Mosior |
| 4,181,131 A | 1/1980 | Ogiu |
| 4,184,492 A | 1/1980 | Meinke |
| 4,200,104 A | 4/1980 | Harris |

(Continued)

FOREIGN PATENT DOCUMENTS

DE　　1139927　　8/1961
(Continued)

*Primary Examiner* — Michael Peffley
*Assistant Examiner* — Daniel Fowler
(74) *Attorney, Agent, or Firm* — Neugeboren O'Dowd PC

(57) ABSTRACT

An electrical switching system for use in various types of electrosurgical instruments and related tools comprises a system adapted to automatically determine which of at least two electrical current modes to deliver through an electrosurgical instrument based on a condition sensed by the electrosurgical instrument. In another embodiment, the electrical switching system comprises a generator, the generator including a first electrical distribution systems for delivering monopolar electrical energy, and a second electrical distribution system for delivering bipolar electrical energy, a controller coupled to the generator for selecting based on an input which of the first and second electrical distribution systems to activate.

32 Claims, 12 Drawing Sheets

U.S. PATENT DOCUMENTS

| | | |
|---|---|---|
| 4,231,372 A | 11/1980 | Newton et al. |
| 4,232,676 A | 11/1980 | Herczog |
| 4,237,887 A | 12/1980 | Gonser |
| 4,248,716 A | 2/1981 | LaValley |
| 4,303,073 A | 12/1981 | Archibald |
| 4,311,144 A | 1/1982 | Harada |
| 4,325,374 A | 4/1982 | Komiya |
| 4,343,308 A | 8/1982 | Gross |
| 4,367,746 A | 1/1983 | Derechinsky |
| 4,374,517 A | 2/1983 | Hagiwara |
| 4,427,006 A | 1/1984 | Nottke |
| 4,433,687 A | 2/1984 | Burke et al. |
| 4,440,170 A | 4/1984 | Golden et al. |
| 4,449,532 A | 5/1984 | Storz |
| 4,494,541 A | 1/1985 | Archibald |
| 4,562,838 A | 1/1986 | Walker |
| 4,569,345 A * | 2/1986 | Manes .................. 606/38 |
| 4,581,021 A | 4/1986 | Landau et al. |
| 4,601,710 A | 7/1986 | Moll |
| 4,615,330 A | 10/1986 | Nagasaki et al. |
| 4,617,927 A | 10/1986 | Manes |
| 4,618,885 A | 10/1986 | Nagasaki et al. |
| 4,638,802 A | 1/1987 | Okada |
| 4,662,369 A | 5/1987 | Ensslin |
| 4,674,501 A | 6/1987 | Greenberg |
| 4,716,897 A | 1/1988 | Noguchi et al. |
| 4,719,914 A | 1/1988 | Johnson |
| 4,744,361 A | 5/1988 | Karasawa |
| 4,781,175 A | 11/1988 | McGreevy et al. |
| 4,787,891 A | 11/1988 | Levin et al. |
| 4,800,869 A | 1/1989 | Nakajima |
| 4,818,954 A | 4/1989 | Flachenecker |
| 4,832,048 A | 5/1989 | Cohen |
| 4,844,063 A | 7/1989 | Clark |
| 4,886,505 A | 12/1989 | Haynes |
| 4,919,129 A | 4/1990 | Weber et al. |
| 4,932,952 A | 6/1990 | Wojciechowicz |
| 4,983,456 A | 1/1991 | Iwaskow |
| 4,998,933 A | 3/1991 | Eggers et al. |
| 5,009,643 A | 4/1991 | Reich et al. |
| 5,009,656 A | 4/1991 | Reimels |
| 5,084,045 A | 1/1992 | Helenowski |
| 5,087,257 A | 2/1992 | Farin et al. |
| 5,089,002 A | 2/1992 | Kirwan |
| RE33,925 E | 5/1992 | Bales et al. |
| 5,116,353 A | 5/1992 | Green |
| 5,147,357 A | 9/1992 | Rose et al. |
| 5,152,762 A | 10/1992 | McElhenney |
| 5,176,702 A | 1/1993 | Bales et al. |
| 5,178,620 A | 1/1993 | Eggers et al. |
| 5,263,967 A | 11/1993 | Lyons et al. |
| 5,275,615 A | 1/1994 | Rose |
| 5,277,696 A | 1/1994 | Hagen |
| 5,281,216 A | 1/1994 | Klicek |
| 5,295,993 A | 3/1994 | Green |
| 5,308,358 A | 5/1994 | Bond et al. |
| 5,312,401 A | 5/1994 | Newton |
| 5,334,198 A | 8/1994 | Hart et al. |
| 5,342,357 A | 8/1994 | Nardella |
| 5,344,428 A | 9/1994 | Griffiths |
| 5,366,443 A | 11/1994 | Eggers et al. |
| 5,383,876 A | 1/1995 | Nardella |
| 5,396,900 A | 3/1995 | Slater et al. |
| 5,403,311 A | 4/1995 | Abele et al. |
| 5,419,767 A | 5/1995 | Eggers et al. |
| 5,423,811 A | 6/1995 | Imran et al. |
| 5,431,638 A | 7/1995 | Hennig |
| 5,443,463 A | 8/1995 | Stern et al. |
| 5,496,317 A | 3/1996 | Goble et al. |
| 5,514,129 A * | 5/1996 | Smith .................. 606/40 |
| 5,520,685 A | 5/1996 | Wojciechowicz |
| 5,531,676 A | 7/1996 | Edwards |
| 5,540,682 A * | 7/1996 | Gardner et al. .................. 606/37 |
| 5,558,671 A | 9/1996 | Yates |
| 5,571,137 A | 11/1996 | Marlow et al. |
| 5,599,350 A | 2/1997 | Schulze et al. |
| 5,609,601 A | 3/1997 | Kolesa et al. |
| 5,626,608 A | 5/1997 | Cuny et al. |
| 5,674,220 A | 10/1997 | Fox et al. |
| 5,683,366 A | 11/1997 | Eggers et al. |
| 5,688,269 A | 11/1997 | Newton et al. |
| 5,688,270 A | 11/1997 | Yates et al. |
| 5,693,051 A | 12/1997 | Schulze et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,709,680 A | 1/1998 | Yates et al. |
| 5,720,744 A | 2/1998 | Eggleston et al. |
| 5,731,896 A | 3/1998 | Baumann et al. |
| 5,735,849 A | 4/1998 | Baden et al. |
| 5,772,659 A | 6/1998 | Becker et al. |
| 5,776,130 A | 7/1998 | Buysse et al. |
| 5,797,941 A | 8/1998 | Schulze et al. |
| 5,800,449 A | 9/1998 | Wales |
| 5,817,093 A | 10/1998 | Williamson et al. |
| 5,827,271 A | 10/1998 | Buysse et al. |
| 5,833,690 A | 11/1998 | Yates et al. |
| 5,911,739 A * | 6/1999 | Kordis et al. .................. 607/122 |
| 5,954,686 A | 9/1999 | Garito et al. |
| 5,976,128 A | 11/1999 | Schilling et al. |
| 6,001,096 A | 12/1999 | Bissinger et al. |
| 6,024,741 A | 2/2000 | Williamson et al. |
| 6,039,732 A | 3/2000 | Ichikawa et al. |
| 6,059,781 A | 5/2000 | Yamanashi et al. |
| 6,086,586 A | 7/2000 | Hooven |
| 6,142,992 A * | 11/2000 | Cheng et al. .................. 606/34 |
| 6,174,309 B1 | 1/2001 | Wrublewski et al. |
| 6,228,080 B1 | 5/2001 | Gines |
| 6,228,083 B1 | 5/2001 | Lands et al. |
| 6,238,388 B1 | 5/2001 | Ellman et al. |
| 6,273,887 B1 | 8/2001 | Yamauchi et al. |
| 6,398,779 B1 | 6/2002 | Buysse et al. |
| 6,409,728 B1 | 6/2002 | Ehr et al. |
| 6,436,096 B1 | 8/2002 | Hareyama |
| 6,440,130 B1 | 8/2002 | Mulier et al. |
| 6,451,018 B1 | 9/2002 | Lands et al. |
| 6,458,130 B1 | 10/2002 | Frazier et al. |
| 6,500,176 B1 | 12/2002 | Truckai et al. |
| 6,506,208 B2 | 1/2003 | Hunt et al. |
| 6,511,476 B2 | 1/2003 | Hareyama |
| 6,582,451 B1 | 6/2003 | Marucci et al. |
| 6,585,735 B1 | 7/2003 | Frazier et al. |
| 6,620,157 B1 | 9/2003 | Dabney et al. |
| 6,682,527 B2 | 1/2004 | Strul |
| 6,682,528 B2 | 1/2004 | Frazier et al. |
| 6,695,840 B2 | 2/2004 | Schulze |
| 6,730,080 B2 | 5/2004 | Harano et al. |
| 6,733,498 B2 | 5/2004 | Paton et al. |
| 6,743,230 B2 | 6/2004 | Lutze et al. |
| 6,767,349 B2 | 7/2004 | Ouchi |
| 6,796,981 B2 | 9/2004 | Wham et al. |
| 6,802,843 B2 | 10/2004 | Truckai et al. |
| 6,827,717 B2 | 12/2004 | Brommersma |
| 6,830,569 B2 | 12/2004 | Thompson et al. |
| 6,855,142 B2 | 2/2005 | Harano et al. |
| 6,890,331 B2 | 5/2005 | Kristensen |
| 6,905,497 B2 | 6/2005 | Truckai et al. |
| 6,929,641 B2 | 8/2005 | Goble et al. |
| 6,929,644 B2 | 8/2005 | Truckai et al. |
| 6,984,231 B2 | 1/2006 | Goble et al. |
| 7,011,657 B2 | 3/2006 | Truckai et al. |
| 7,052,496 B2 | 5/2006 | Yamauchi |
| 7,083,618 B2 | 8/2006 | Couture et al. |
| 7,083,619 B2 | 8/2006 | Truckai et al. |
| 7,089,054 B2 | 8/2006 | Palti |
| 7,090,673 B2 | 8/2006 | Dycus et al. |
| 7,094,231 B1 | 8/2006 | Ellman et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,199 B2 | 9/2006 | Cosmescu |
| 7,112,201 B2 | 9/2006 | Truckai et al. |
| 7,115,121 B2 | 10/2006 | Novak |
| 7,118,587 B2 | 10/2006 | Dycus et al. |
| 7,131,445 B2 | 11/2006 | Amoah |
| 7,131,971 B2 | 11/2006 | Dycus et al. |

| | | |
|---|---|---|
| 7,135,020 B2 | 11/2006 | Lawes et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,300 B2 | 12/2006 | Goble |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,186,253 B2 | 3/2007 | Truckai et al. |
| 7,186,261 B2 | 3/2007 | Prestel |
| 7,189,233 B2 | 3/2007 | Truckai et al. |
| 7,195,631 B2 | 3/2007 | Dumbauld |
| 7,203,556 B2 | 4/2007 | Daners |
| 7,204,835 B2 | 4/2007 | Latterell et al. |
| 7,207,990 B2 | 4/2007 | Lands et al. |
| 7,211,081 B2 | 5/2007 | Goble |
| 7,211,084 B2 | 5/2007 | Goble et al. |
| 7,214,224 B2 | 5/2007 | Charles et al. |
| 2002/0049483 A1* | 4/2002 | Knowlton .................. 607/101 |
| 2002/0120260 A1* | 8/2002 | Morris et al. ................. 606/41 |
| 2002/0165541 A1 | 11/2002 | Whitman |
| 2003/0073987 A1 | 4/2003 | Sakurai et al. |
| 2004/0193148 A1 | 9/2004 | Wham et al. |
| 2005/0021027 A1 | 1/2005 | Shields et al. |
| 2005/0113827 A1 | 5/2005 | Dumbauld et al. |
| 2005/0131390 A1 | 6/2005 | Heinrich et al. |
| 2005/0137590 A1 | 6/2005 | Lawes et al. |
| 2005/0187539 A1* | 8/2005 | Takahashi .................... 606/1 |
| 2005/0187547 A1 | 8/2005 | Sugi |
| 2005/0203504 A1 | 9/2005 | Wham et al. |
| 2005/0256522 A1 | 11/2005 | Francischelli et al. |
| 2006/0079876 A1 | 4/2006 | Houser et al. |
| 2006/0129146 A1 | 6/2006 | Dycus et al. |
| 2006/0167450 A1 | 7/2006 | Johnson et al. |
| 2006/0173452 A1 | 8/2006 | Buysse et al. |
| 2006/0224158 A1 | 10/2006 | Odom et al. |
| 2006/0293656 A1 | 12/2006 | Shadduck et al. |
| 2007/0043353 A1 | 2/2007 | Dycus et al. |
| 2007/0066969 A1 | 3/2007 | McGreevy et al. |
| 2007/0078456 A1 | 4/2007 | Dumbauld et al. |
| 2007/0106297 A1 | 5/2007 | Dumbauld et al. |

FOREIGN PATENT DOCUMENTS

| | | |
|---|---|---|
| DE | 3013784 | 10/1980 |
| JP | 52-47278 | 12/1977 |
| JP | 53-13583 | 2/1978 |

* cited by examiner

COMBINED BIPOLAR AND MONOPOLAR ELECTROSURGICAL INSTRUMENT AND METHOD

RELATED CASES AND PRIORITY

This application claims the benefit of Provisional U.S. Patent Application No. 60/804,601 filed on Jun. 13, 2006. The details of Application No. 60/804,601 are incorporated by reference into the present application in their entirety.

FIELD OF THE INVENTION

The present invention relates to electrosurgical instruments and the control of multimodal electrosurgical energy in such instruments. In particular, but not by way of limitation, the present invention relates to systems and methods for selectively delivering both bipolar and monopolar electrical energy through a single electrosurgical instrument.

BACKGROUND OF THE INVENTION

In general, monopolar electrosurgery is the passage of high-frequency current to tissue through a single heating (or active) electrode to a return electrode positioned remotely from the active electrode where heating does not take place. Bipolar electrosurgery is the passage of high frequency current to tissue between two commonly-supported electrodes where both actively heat tissue.

Monopolar configurations are widely used for general cutting and coagulation procedures, usually utilizing applications of energy of 1 to 5 seconds. Monopolar electrosurgery is widely recognized to be ideal for spray coagulation where there is heating across a surface of tissue proximal to an active electrode. The current field will include a large portion of the patient, but will have high current density only near the active electrode.

Bipolar configurations are widely used for procedures such as coagulation and ablation of tissue where a volume of tissue is positioned between two active electrodes and heated for several seconds, or tens of seconds. The current field in a bipolar device is contained within the neighborhood of the two electrodes.

Many surgeons regularly alternate between bipolar and monopolar instruments in a single surgical procedure. For example, an operating room may utilize ValleyLab monopolar generators and a Wolf bipolar generator all stacked on a single equipment cart. In addition, current monitoring systems, such as an Active Electrode Monitor "AEM" made by Encision, Inc. of Boulder, Colo., may also be incorporated into the overall hardware configuration. Such equipment setups are especially common during OB/GYN procedures. Because the change over between the two generators and instruments takes some time and operating room resources, it is desirable to have a single generator/AEM monitor/controller system that utilizes a single specialized instrument capable of operating in either monopolar or bipolar electrical modes. Such an equipment configuration would minimize changeover time or effectively eliminate changeover time altogether. A description of Active Electrode Monitoring can be found in U.S. Pat. No. 5,312,401, the details of which are incorporated by reference in its entirety. Encision, Inc. of Boulder, Colo. manufactures several AEM systems and configurations for use during electrosurgical procedures.

Given that it is preferable for a single generator to be used with an AEM monitor and controller, it is also desirable to avoid processing either the monopolar or the bipolar outputs in order to utilize both electrical modes (e.g. by deriving the bipolar output from the monopolar output). This configuration allows transparent functioning of the generator manufacturer's electrosurgical modes but requires that the two outputs be isolated in order to prevent damage or distortion.

While the presently utilized combinations of devices are functional, they do not provide the ability to quickly and easily switch between bipolar and monopolar modes and cannot avoid using multiple tools and generator hardware to accomplish both types of electrosurgery. Accordingly, a system and method are needed to address the shortfalls of present technology and to provide other new and innovative features.

Exemplary embodiments of the present invention are shown in the drawings and are summarized below in the accompanying description. It is to be understood, however, that there is no intention to limit the invention to the forms described herein. One skilled in the art can recognize that there are numerous modifications, equivalents and alternative constructions that fall within the spirit and scope of the invention as expressed in the claims. Numerous other embodiments, implementations, and details of the invention are easily recognized by those of skill in the art from the following descriptions and claims.

SUMMARY OF THE INVENTION

An electrical switching system for use in various types of electrosurgical instruments and related tools comprises a system adapted to automatically determine which of at least two electrical current modes to deliver through an electrosurgical instrument based on a condition sensed by the electrosurgical instrument.

In another embodiment, an electrical switching system for selectively delivering either bipolar or monopolar electrical energy through a surgical instrument comprises a generator, the generator including a first electrical distribution system for delivering monopolar electrical energy, and a second electrical distribution system for delivering bipolar electrical energy, a controller coupled to the generator for selecting based on an input which of the first and second electrical distribution systems to activate. The controller comprises a first pair of relays actively coupled to the first electrical distribution system, a second pair of relays actively coupled to the second electrical distribution system, a switch for selecting either the first electrical distribution system or the second electrical distribution system, and a keying circuit coupled to the switch for selectively engaging either the first or second electrical distribution systems.

In another embodiment, an electrical connection system for selectively delivering either bipolar or monopolar electrical energy through a surgical instrument comprises a generator including a first electrical distribution system for delivering monopolar electrical energy, and a second electrical distribution system for delivering bipolar electrical energy. The electrical connection system also comprises a controller coupled to the generator for selecting based on an input which of the first and second electrical distribution systems to activate, the controller comprising a first pair of relays electrically coupled to the first electrical distribution system, a second pair of relays electrically coupled to the second electrical distribution system, a switch for selecting either the first electrical distribution system or the second electrical distribution system, a keying circuit coupled to the switch for selectively engaging either the first or second electrical distribution systems, a third set of relays coupled to the first and second set of relays, and an impedance sensing circuit coupled to and disposed between the logic circuit and the third set of relays.

In a further embodiment, a surgical instrument comprises means for selectively delivering either bipolar or monopolar electrical current while also being adapted to utilize a monitoring system such as active electrode monitoring.

Various other embodiments and variations will become evident in conjunction with the attached description and drawing figures. One of skill in the art will easily recognize that the scope of the present invention is not to be limited by the description herein.

BRIEF DESCRIPTION OF THE DRAWINGS

Various objects and advantages and a more complete understanding of the present invention are apparent and more readily appreciated by reference to the following detailed description and to the appended claims when taken in conjunction with the accompanying drawings wherein:

DETAILED DESCRIPTION

Figure 1A:
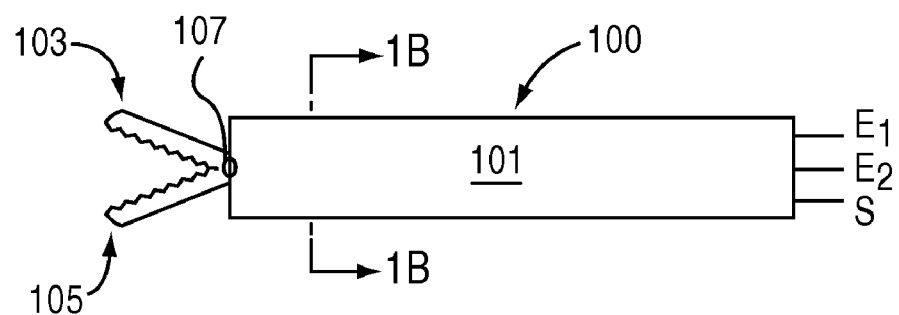
FIG. 1A is a generalized diagram of a device constructed in accordance with one aspect of the present invention.
Figure 1B:
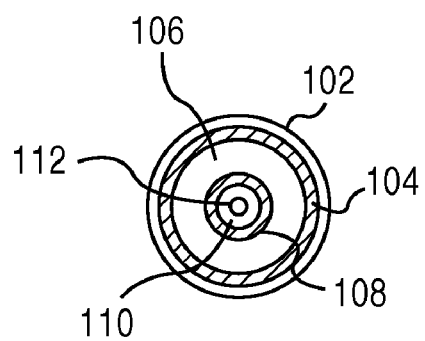
FIG. 1B is a cross section of the diagram of FIG. 1A.

Referring now to the drawings, FIGS. 1A and 1B represent a simplified view of an instrument tube assembly 100 constructed in accordance with one aspect of the present invention. The overall format of instrument tube assembly 100 shown in FIGS. 1A and 1B is typical of many different laparoscopic electrosurgical instruments that are known in the art. FIGS. 1A and 1B are intended to represent various different types of tools that may be used in connection with one or more aspects of the present invention. It is understood that a device constructed in accordance with the present invention can be used in conjunction with many different electrosurgical instruments and in conjunction with many different electrosurgical procedures. Examples include gynecological surgical tools and associated procedures, general surgical tools and associated procedures, various types of thoracoscopy surgical tools and associated procedures, and various other types of surgical tools and procedures that would require the delivery of electrical current and that are known in the art.

In general, the instrument tube assembly 100 comprises a tubular body 101 and a pair of operative jaws 103 and 105 connected at a hinge point 107. Labels $E_1$ and $E_2$ represent first and second electrical conductors coupled with jaws 103 and 105 respectively. S is a shield conductor coupled to a safety shield incorporated into the tube assembly. FIG. 1B is an enlarged cross-section of the instrument tube assembly 100 of FIG. 1A where 102 is an outer insulation layer, 104 is a shield, 106 is a primary insulation layer, 108 is the first conductor depicted as $E_1$ in FIG. 1A, 110 is an insulation layer and 112 is the second conductor $E_2$ depicted in FIG. 1A.

Figure 2:
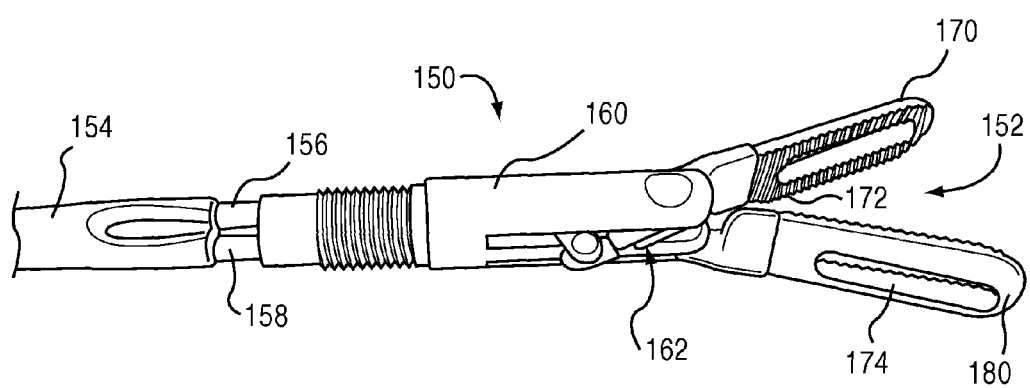
FIG. 2 is an isometric view of a surgical tool incorporating one or more aspects of a device constructed in accordance with the present invention.

FIG. 2 represents a first detailed embodiment of an electrosurgical instrument 150 that includes a hinged jaw structure 152. In one embodiment, an outer metal tube 154 has a diameter that is designed to fit within housing 160 of the instrument tube assembly. Insulation conductor 156 corresponds to conductor E1 in FIG. 1A and insulation conductor 158 corresponds to conductor E2 in FIG. 1A. Each of the conductors 156 and 158 have a preferable diameter that allows them to run parallel to each other through housing 160. Instrument housing 160 is shown broken to reveal the details of the inner components of the instrument 150 but preferably extends away from the jaw structure and to the handle assembly described below. The housing 160 is preferably made of an insulative material such as, for example, poly ether ether ketone (PEEK). The outer metal tube 154 is electrically isolated from both jaws 170 and 180. First jaw 170 and second jaw 180 form the operative portion of the instrument 150 and are the components that deliver electrical energy to the tissue undergoing surgical procedure. Jaws 170 and 180 are hinged and operatively connected by a hinge point 162, which provides actuation ability back to a surgeon or other user via means that are know in the art. The jaws include gripping surfaces 172 and openings 174 in order to provide increased usability and function to the jaw surfaces. In addition, the jaws 170 and 180 are coated with a thin layer of insulation in order to also increase usability. With all of the components described above, various combinations of sizes, tolerances and sizes are contemplated and the examples given above are meant to be illustrative only.

Figure 3:
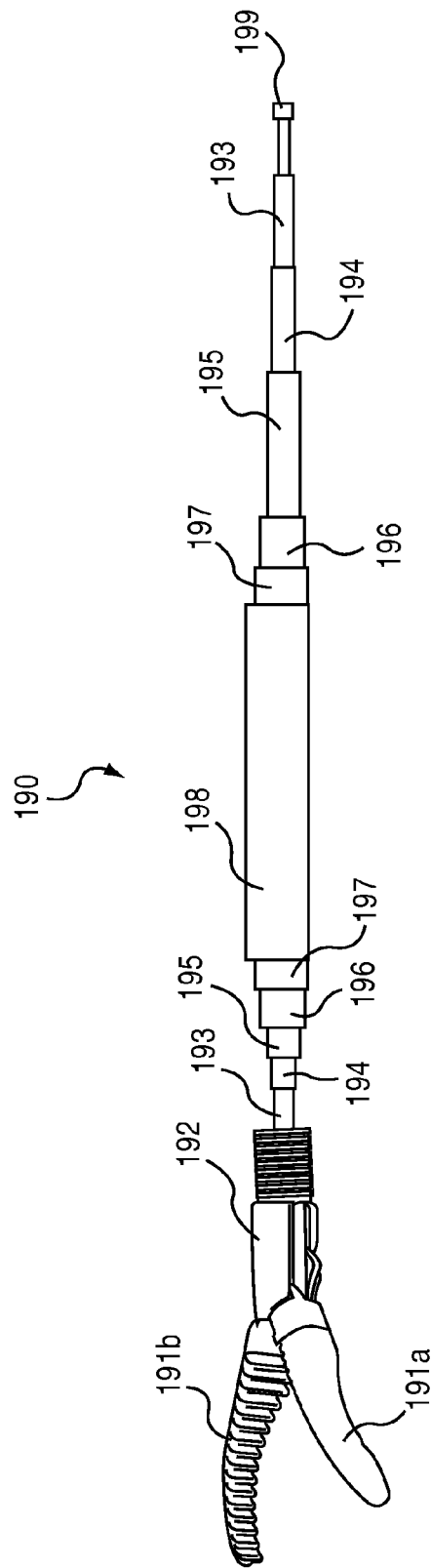
FIG. 3 is an isometric view of another embodiment of a surgical tool incorporating one or more aspects of a device constructed in accordance with the present invention.

In another embodiment constructed in accordance with the present invention, the general instrument structure of FIG. 2 may be constructed in a coaxial manner and include the following modifications and improvements. With reference to FIG. 3, an instrument tube assembly 190 includes pushrod assembly 199, including stepped portion 193 that may be made coaxial so that the assembly is the conductor for one of the jaw tips 191a. Another coaxial metal tube 195 is a conductor for the other jaw tip 191b. The coaxial size of the tube/pushrod may be made to be approximately equal to the pushrods in currently available systems such as the Encision, Inc. 5700/8000 instrument. In FIG. 3, 198 represents the outer insulator, 197 represents the shield tube, 196 represents a second insulator, 194 represents a first insulator, and 192 represents a non-conductive portion of the instrument housing.

In accordance with one aspect of a device constructed in accordance with the present invention, a electrical connection scheme and system for coupling the monopolar and bipolar outputs of a generator to an instrument generally comprises a process and structure that effectively isolates the monopolar and bipolar outputs while also eliminating the need to drive the unused generator output through a controller. One embodiment of such a connection scheme s shown in FIG. 4.

Figure 4:
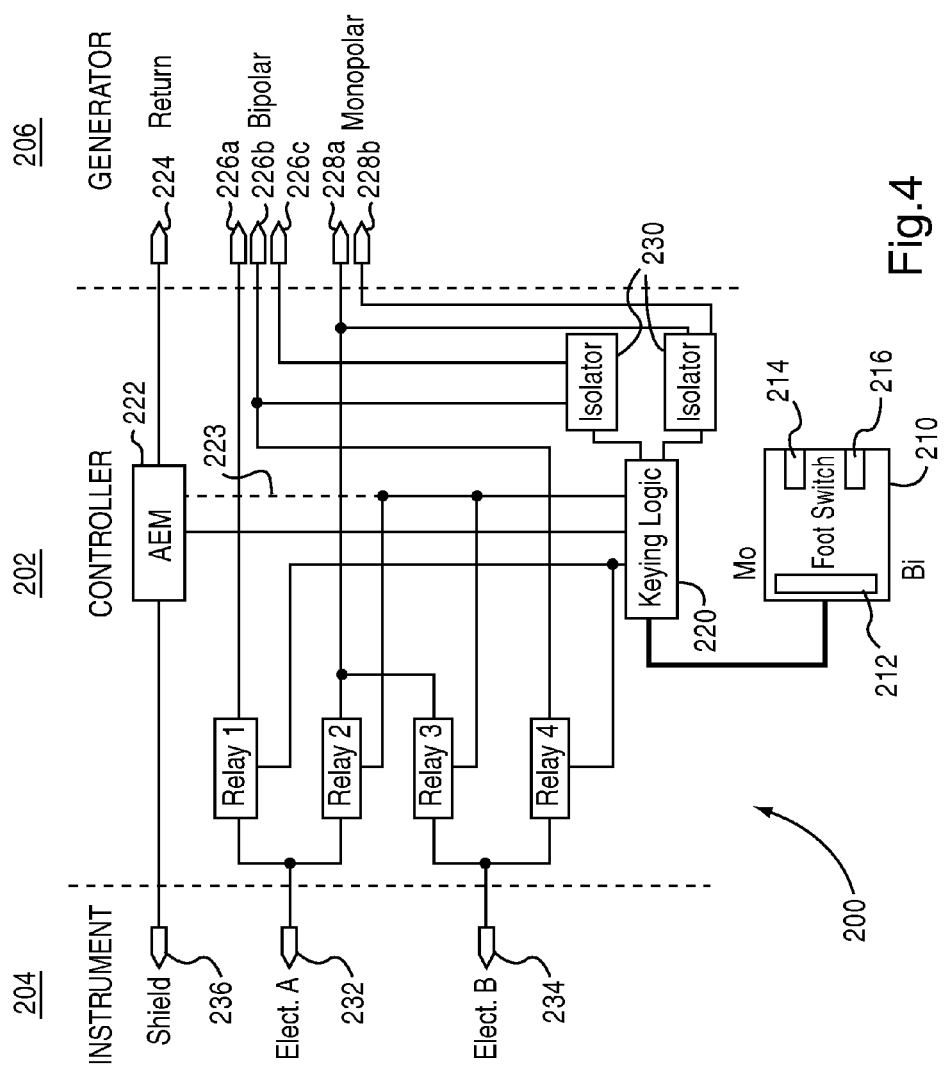
FIG. 4 is a schematic diagram of a connection scheme in accordance with an aspect of the present invention.

With further reference to FIG. 4, a first aspect and embodiment of a bipolar-monopolar, or otherwise multi-modal, connection device 200 constructed in accordance with the present invention is described. FIG. 4 illustrates a device where three general components are utilized to create a system that enables switching between a first and second electrosurgical mode. In a preferred embodiment, the first and second electrosurgical modes and bipolar and monopolar electrosurgical current. A controller module 202 includes four relays that control the flow of electrical energy from a generator 206 to an instrument 204. In operation, relays 1 and 4 are switched closed for the delivery of bipolar energy and relays 2 and 3 are switched closed for the delivery of monopolar energy. This provides for the switching of current flow from the generator 206 between a bipolar and monopolar mode based on a switch position enabled by a user. For example, a footswitch 210 with a monopolar bipolar selector/treadle 212 is connected to the controller module 202. The foot switch 210 includes cut and coagulation selectors 214 and 216 which are additional operated via the user. The generator 206 is preferably keyed via hand switching outputs by isolating switching circuits 230 and keying logic circuits 220 located in the control module 202. Separate connections are maintained within generator 206 for the distribution of either bipolar current, e.g connectors 226a-c, or for the distribution of monopolar current, e.g. connectors 228a-b. The instrument 204 includes mechanisms for the distribution of the bipolar and monopolar current via the conductors 232 and 234. A shield sensor 236 couples back to the generator 206 preferably through an Active Electrode Monitoring ("AEM") system 222 in order to provide a monitored system and to shut off the delivery of electrical current in the case of a fault condition. AEM circuitry is adapted to work in combination with the delivery of either bipolar or monopolar current. The relays may be any of various known relays including high voltage reed relays, field effect transistor (FET) relays, and solid state relays.

The AEM system 222 is preferably one that is known in the art and may operate with its own current processing. Alternately, through a connection 223, a voltage reference can additionally be read in order to ascertain a phase comparison. These monitoring techniques may be used independently or in conjunction with each other in order to provide feedback to the generator 206 and to shut down the flow of current upon the occurrence of a fault condition. The operation of the AEM system 222 can be accomplished by known means, for example as described in U.S. Pat. No. 5,312,401 or as implemented in the AEM devices sold by Encision, Inc.

The schematic diagram of FIG. 4 is meant to be illustrative of the various interconnections made in the described system. One of skill in the art would understand the many possible variations available to effect the interconnections depicted in FIG. 4, including the choice of materials and components.

As described above, in one embodiment the control of monopolar and bipolar modes is accomplished via a footswitch 210. The footswitch 210 preferably houses an additional treadle 212 compared to the nominal cut/coagulation selection treadles 214 and 216 in order enable a user to switch between the monopolar and bipolar modes. An alternate means of monopolar/bipolar control contemplated by the present invention is to provide a front panel control switch located on the generator being used as the monitor/controller. Such a controller scheme may also be combined with an automated sensing feature that senses the conditions at the tines (jaw) of the instrument in order to produce the desired tissue effects. The table below represents one such algorithm used for automatic selection of monopolar and bipolar operation. Such an algorithm may be implemented in software, hardware, firmware, or another means as is known in the art.

| Bipolar-Monopolar Switch Conditions | | |
| --- | --- | --- |
| Mode | Switch | Conditions |
| Monopolar | Mono | Unconditional |
| BiMono | Auto | If (x > z > y) then Bipolar; If (z ≧ x or z ≦ y) then Monopolar |
| Bipolar | Bipolar | Unconditional |

Where:
z is measured impedance just prior to activation
x is a high limit of impedance (~500 ohms)
y is a low limit of impedance (~20 ohms)

Thus, as seen from the above data, bipolar functionality is selected if tissue is positioned across the instrument jaws.

In order to alert a user as to which type of energy is currently active, it is preferable to have the generator or controller generate a distinctive audible tone or tone sequence that indicates the mode that is active or that indicates that a particular mode is about to be activated. For example, upon activation of monopolar current, a continuous tone would be heard where upon activation of bipolar current, a repeating tone would be heard. Other audible schemes are contemplated and visual indicators may also be included on the generator, controller, or instrument itself to alert the user as to the type of RF energy that is currently active within the device.

Figure 5:
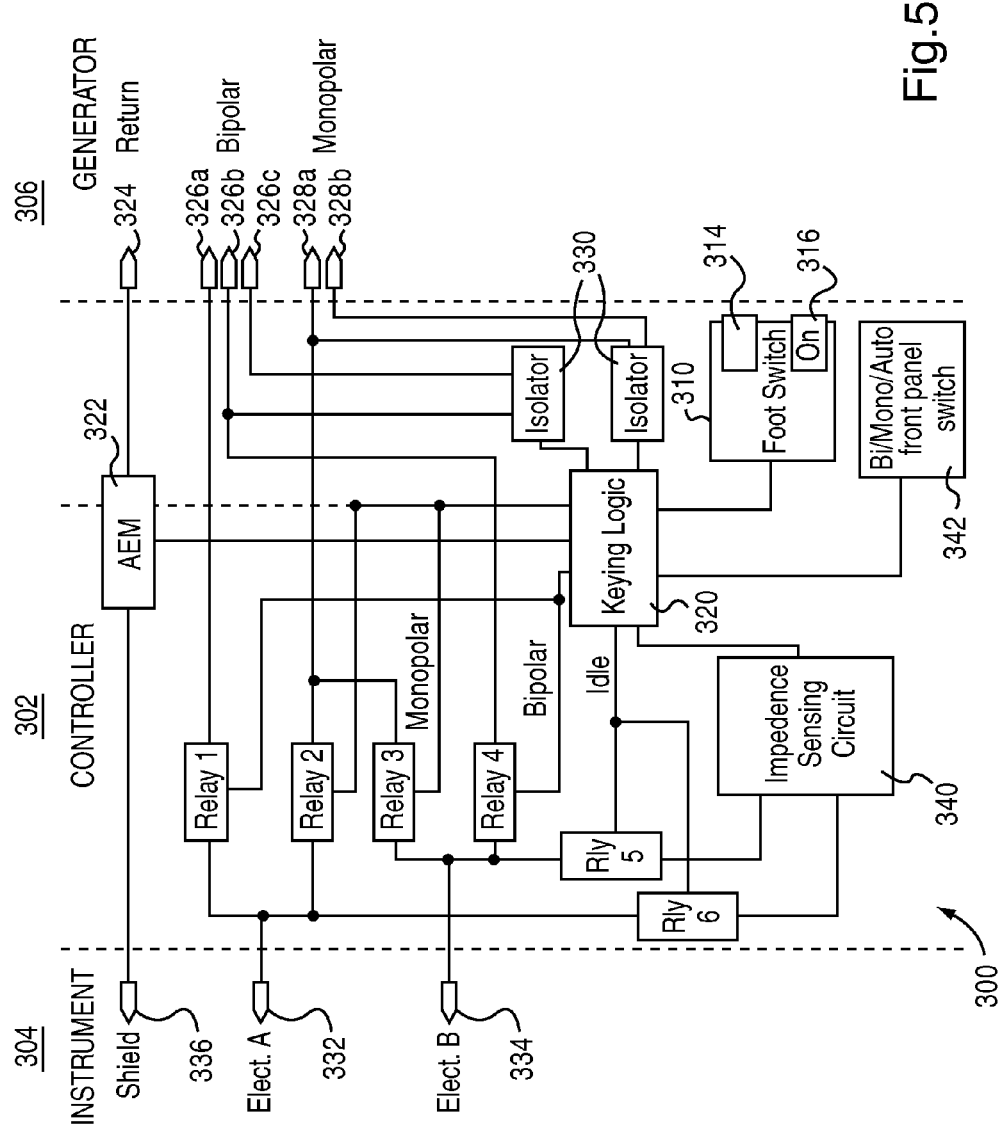
FIG. 5 is a schematic diagram of a connection scheme in accordance with another aspect of the present invention.

In other embodiments, the controller has a load impedance sensor that is active at least in the RF idle state, but could also be active in the RF active state as well. Such an impedance sensor operates on the load impedance between the jaws of the grasper and preferably makes measurements every few tenths of a second. In a preferred implementation, the monopolar/bipolar switch sensing is accomplished in the idle state just prior to RF activation. FIG. 5 is diagrammatic embodiment of a monopolar/bipolar circuit 300 contemplated by a device constructed in accordance with the present invention. Differences between the circuit shown in FIG. 5 and the one previously shown in FIG. 4 include the addition of an impedance sensing circuit 340, the addition of relays 5 and 6, and the inclusion of a front panel switch 342. In FIG. 5, the instrument 304, generator 306, relays 1-4, AEM unit 322, keying logic 320, isolators 330, and foot switch 310 have the same characteristics as the similarly described components of FIG. 4.

In FIG. 5, the impedance sensing circuit 340 preferably has a range of ~10 ohms to 1000 ohms, repeatability of ~±3Ω or 2% of reading, immunity from radio frequency interference (RFI) generated by nominal electrosurgical currents, and a frequency of approximately 100 kHz, which is above the nerve stimulation range.

While various embodiments of the impedance sensing circuit 340 are contemplated, as an example, the circuits disclosed in U.S. Pat. No. 4,416,277 (shown as FIG. 6) would likely meet these needs. However, in accordance with an aspect of the present invention, an adjustment is made to the circuit for the range exhibited by normal electrosurgical return electrodes. These measurements are approximately 5-150Ω. Also, output sensing of the measured impedance compared to the x and y of thresholds needs to be added. In this embodiment, the gate produces a logic low if z is within range for bipolar, otherwise the output is high for monopolar.

Figure 6:
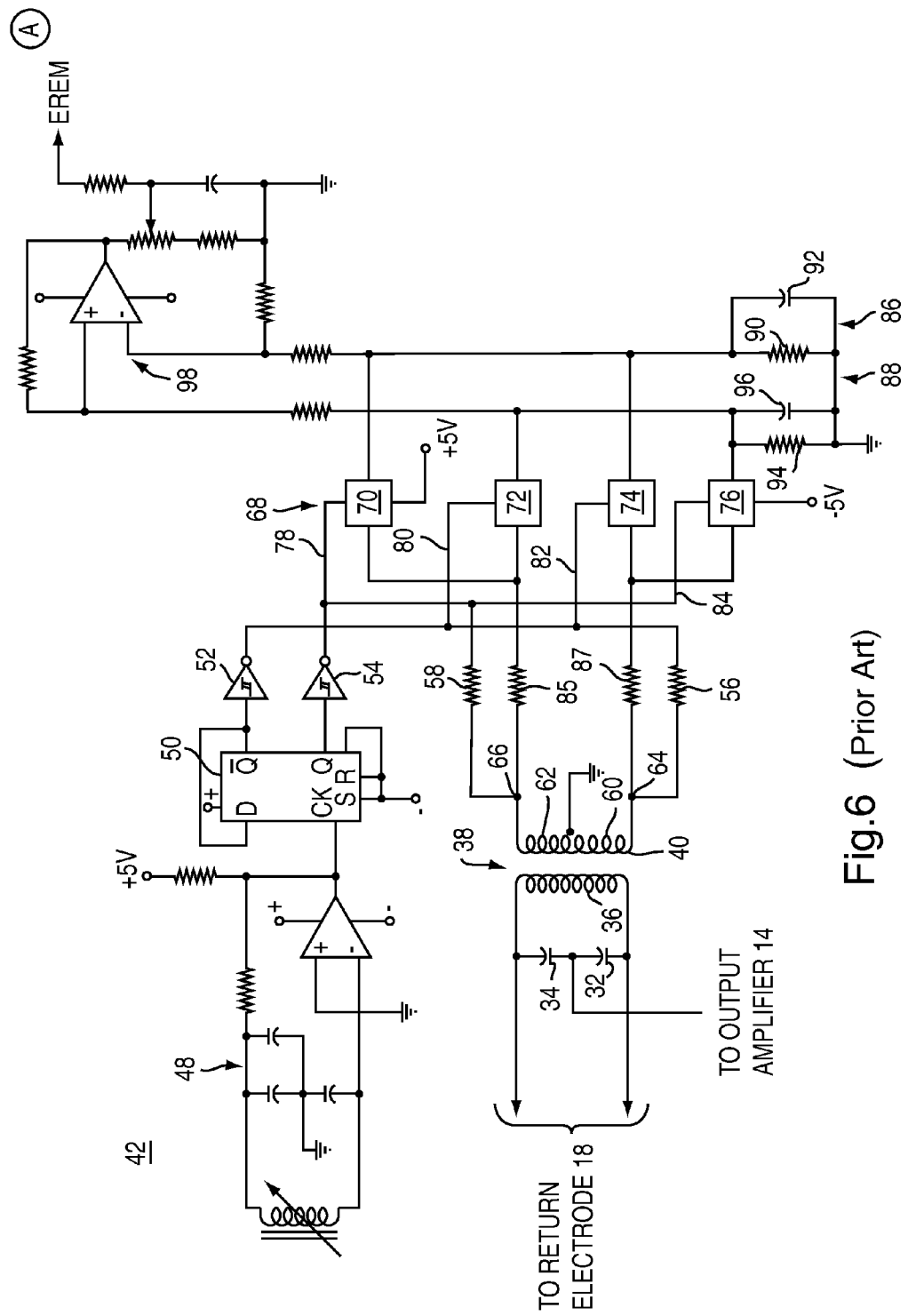
FIG. 6 is a prior art impedance sensing circuit.
Figure 7:
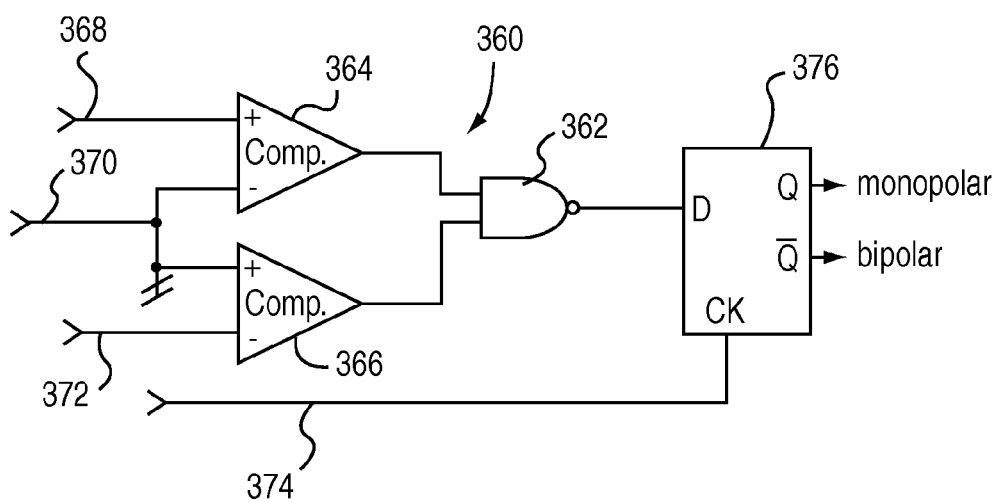
FIG. 7 is a logic circuit constructed in accordance with an aspect of the present invention.

For example, approximately 30 ms prior to RF activation the data presented to flip-flop "A" in FIG. 6 would be clocked by a strobe signal from the control keying logic. (This is approximately the same as the time the relays need to be driven to their new state.) An example of this embodiment as contemplated in accordance with an aspect of the present invention is shown in FIG. 7 which would replace the embodiment of flip flop "A" shown in FIG. 6. In FIG. 7, threshold impedance sensor 360 includes impedance input 370, high threshold 368 and low threshold 372 in communication with a pair of comparators 364 and 366. The comparators 364 and 366 are coupled to NAND gate 362 which is in turn coupled to a DFLOP 376. Clock 374 also inputs to the DFLOP 376 for control purposes. DFLOP 376 then determines whether to engage the monopolar mode or the bipolar mode via an electrosurgical generator.

Figure 8:
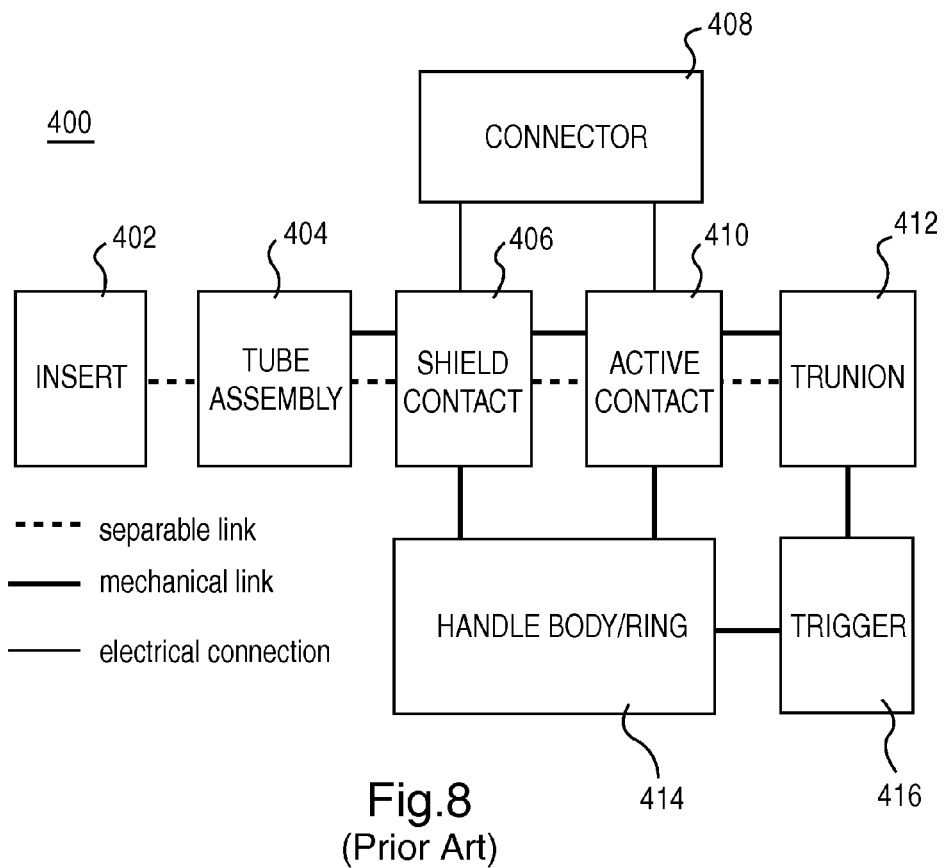
FIG. 8 is a block diagram of a prior art electrosurgical instrument.
Figure 9:
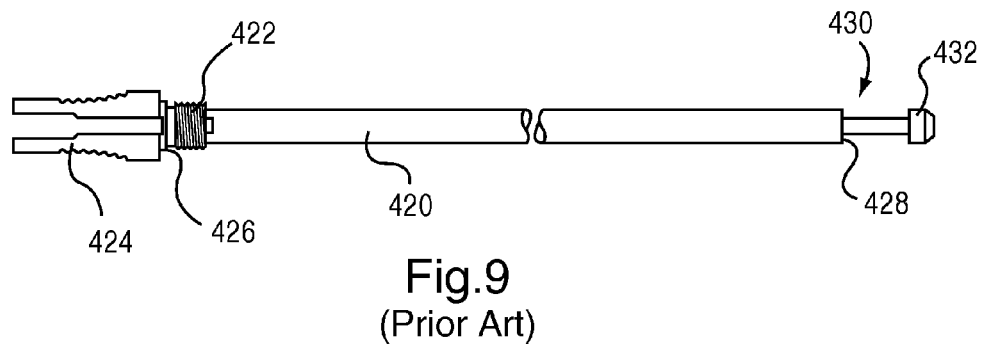
FIG. 9 is a physical representation of the insert depicted in FIG. 8.

FIG. 8 represents a block diagram showing the major components of a typical AEM instrument 400, where a replaceable insert 402 attaches at the distal end of a tube assembly 404 and projects through the tube and into a handle body/ring assembly 414. The insert 402 makes electrical contact with an active contact 410 and mechanical drive attachment at the trunion 412, a component of the trigger 416. Connector 408 engages shield contact 406 with the active contact 410. The insert 402 may be reusable or a disposable (singular use) device. An example of this type of construction is detailed in U.S. Pat. No. 6,494,877 which is incorporated by reference in its entirety. For example, and as shown in FIG. 9, item 420 is a conductive shaft that passes through the active contact. Items 428, 430, and 432 make connection with the trunion. Threads 422 connect to the tube assembly.

Figure 10A:
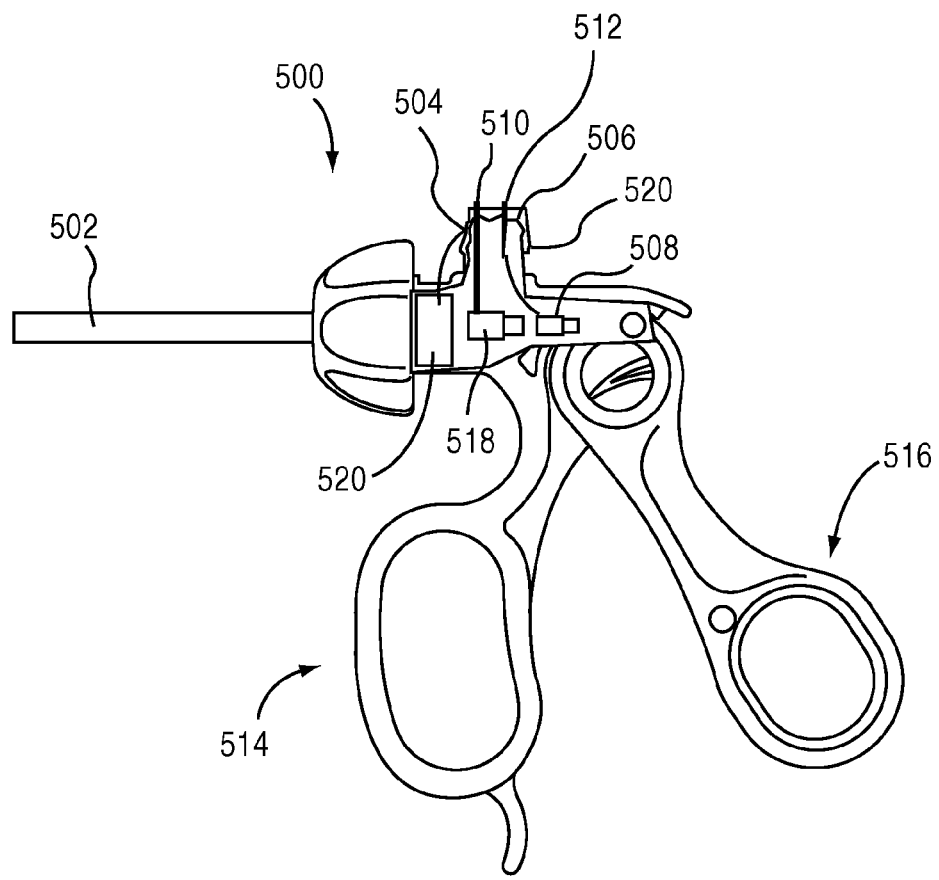
FIG. 10A is a handle assembly constructed in accordance with one aspect of the present invention.

FIG. 10A is a side view of an AEM instrument 500. In the assembly 500, 502 is a tube assembly, 504 is a shield contact, 506 is a connector, 508 is an active contact, 510 is an active pin, 512 is another active pin, 514 is the handle body and 516 is a trigger mechanism. For a monopolar/bipolar instrument constructed in accordance with one aspect of the present invention, an active contact 518 and enlarged connector 520 are added to support the additional conductor of the second active contact.

Figure 10B:
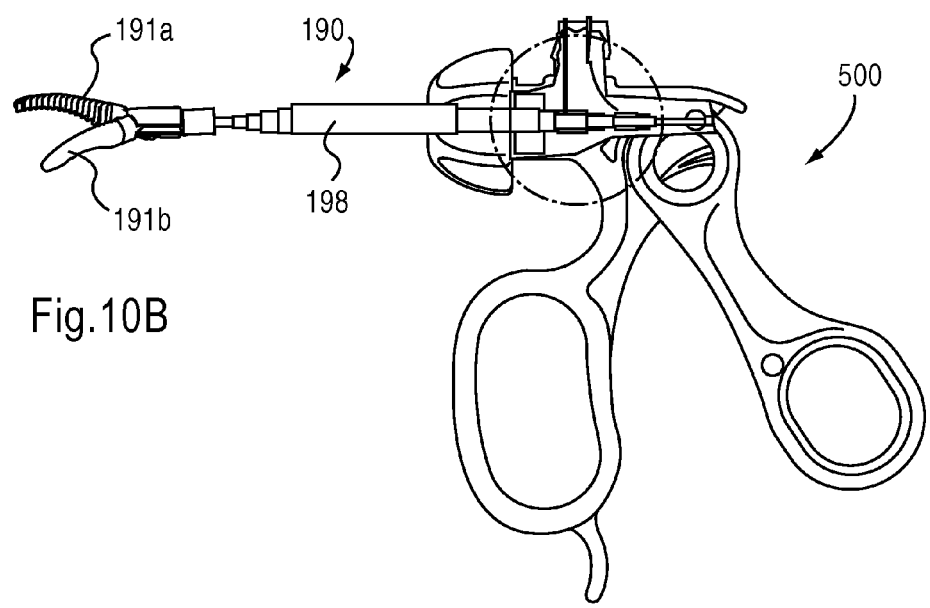
FIGS. 10B-10C show further details of the handle assembly of FIG. 10A.
Figure 10C:
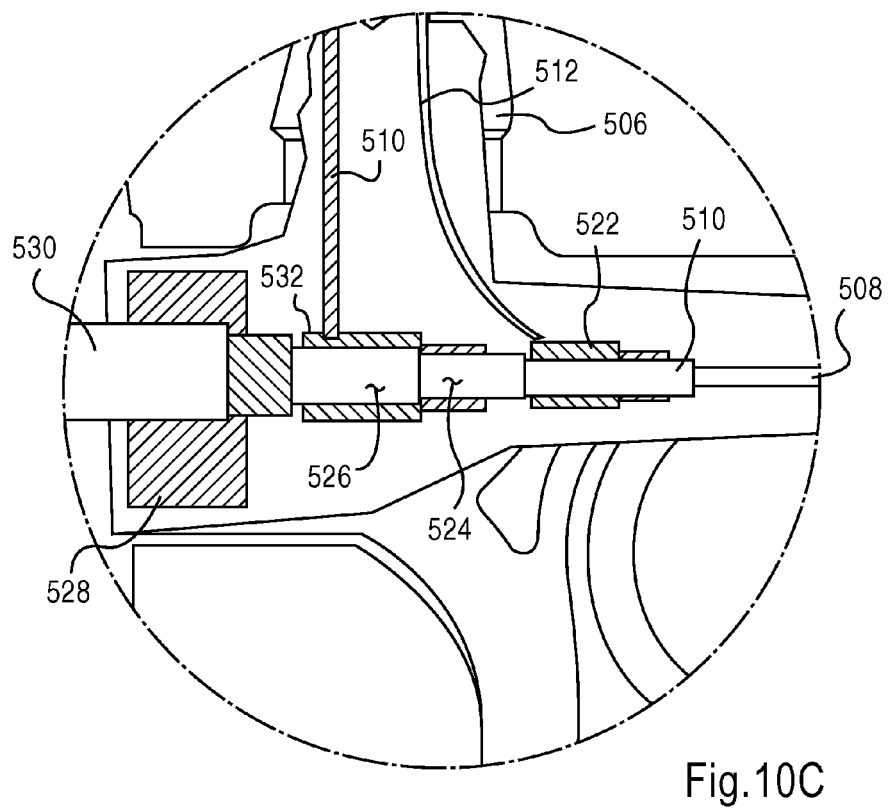

FIGS. 10B-10C include further details of the AEM instrument 500 handle assembly and its interconnection with an instrument tube assembly 190 as described in one or more of the above embodiments, such as FIG. 3. FIGS. 10B and 10C show the details of the interconnection between the instrument tube assembly 190 and the instrument handle assembly 500, and specifically how the instrument tube assembly 190 makes electrical contact with the handle assembly 500 via active pin connectors 510 and 512 which connect to electrical contacts 522 and 532 within handle assembly 500 and engage with active elements 526 and 510 on the instrument tube assembly. Shield 530 on the instrument tube assembly engages with shield connector 528.

Figure 11:
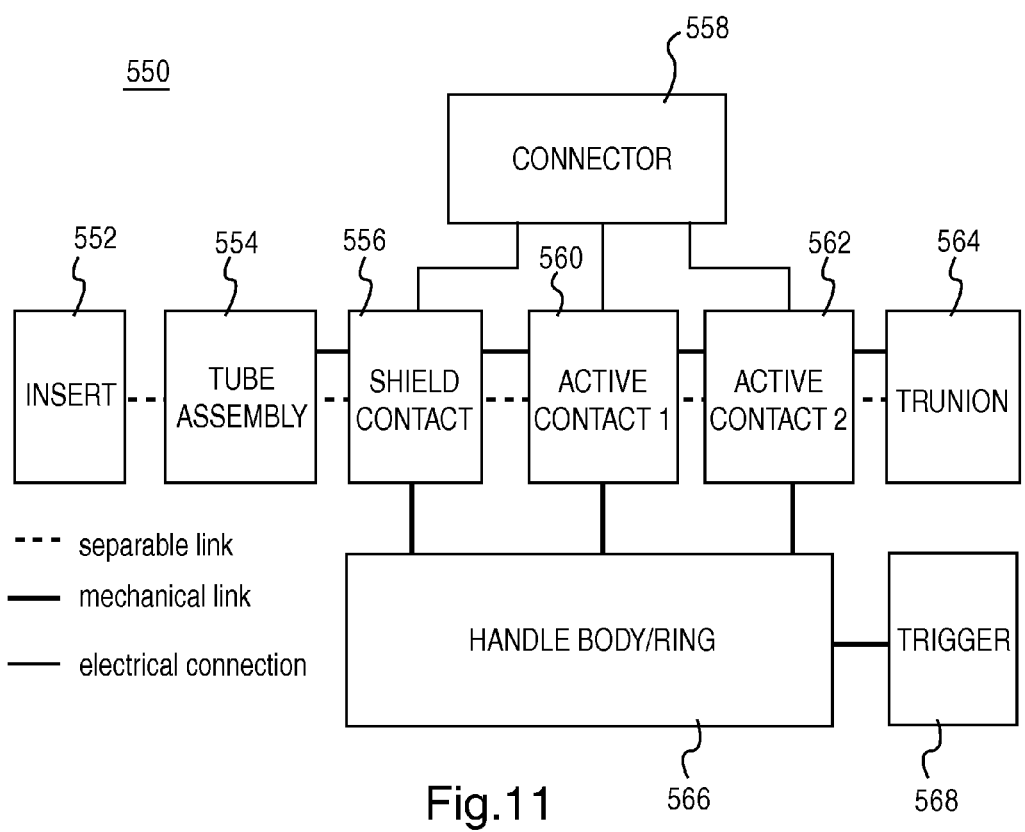
FIG. 11 is a block diagram of an electrosurgical instrument constructed in accordance with one aspect of the present invention.

FIG. 11 is a block diagram of a device constructed in accordance with one or more aspects of the present invention which includes more than one active contact to enable the delivery of both monopolar and bipolar electrical energy. In FIG. 11, a dual mode device 550 includes a disposable insert 552 coupled with a tube assembly 554, a shield contact 556, a first active contact 560 and at least a second active contact 562. The device further includes an electrical connector 558 that is sized to support the additional conductor associated with active contact 562, a trunion 564, a handle body 566 and a trigger mechanism 568. The block diagram of FIG. 11 shows the general relationship of the components included in such a device. Based on this general layout, one of skill in the art would recognize how to interconnect the various components using conventional design and manufacturing techniques.

In accordance with the above and with various aspects of the present invention, a bipolar/monopolar electrosurgical device may be used in a variety of way an in conjunction with many different surgical procedures. For example in a laparoscopically assisted vaginal hysterectomy (LAVH), bipolar functionality would be used for taking down the broad ligament and sealing the uterine arteries. Monopolar functionality would be used for the general control of bleeding in transected tissue including coagulation of capillary bleeding.

Bipolar devices, as opposed to monopolar devices, typically exhibit more friction in the operation of the inserts and are often perceived as requiring a high force to actuate. The increased force required results from a combination of several factors, including the geometry of the handle, the geometry of the tip linkage and friction with the system. This can be attributed to, among other potential issues, the fact that insulation in bipolar jaw structures tend to contribute to mechanical interference and thus increased friction. Also, the dual active contacts required increase the sliding friction with the insert. To mitigate this increased friction, a device constructed in accordance with the present invention preferably includes one or two active contacts that involve a highly flexible wire 612 and a self-positioning sliding interface 604 as shown in conjunction with FIG. 12.

These friction problems may also be solved in one or more of the following ways. First, by relieving interference through appropriate design of the housing tolerances and interaction of the internal components. Second, by controlling the dimensions of the jaw contact blades, sliding friction may be reduced. Third, by specially designing the contacts so that have very low friction themselves. For example, this can be accomplished by eliminating the sliding interface between the contact and the insert assembly and allowing the contact member to float longitudinally with electrical conduction performed by a flexible wire. This method greatly reduces the friction in the system.

Figure 12:
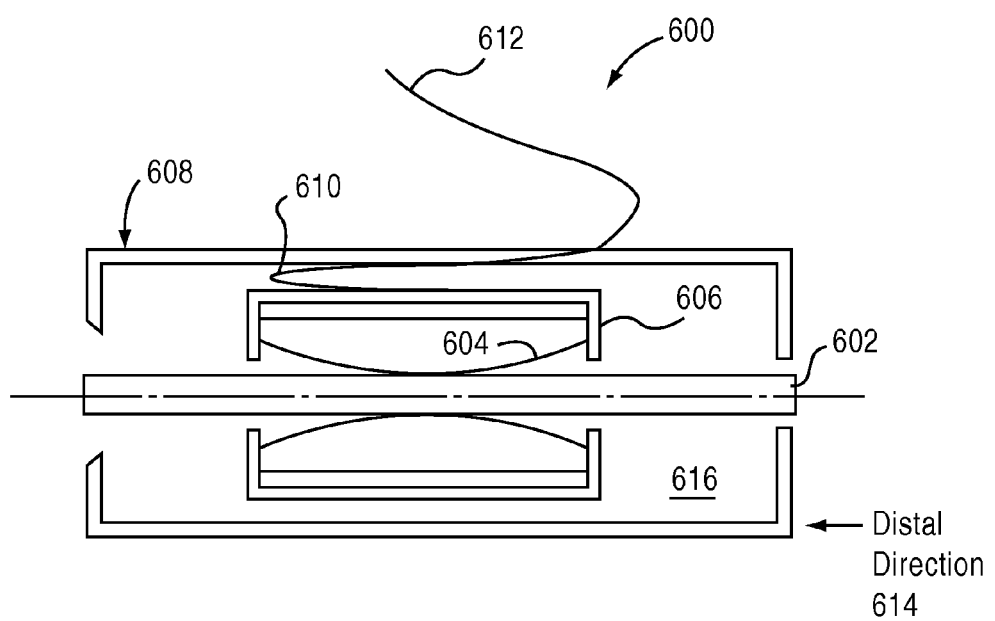
FIG. 12 is a diagrammatic representation of a contact device constructed in accordance with an aspect of the present invention.

A solution in accordance with one aspect of the present invention allows the contact to fit snugly within the housing and around the rod while also allowing the housing to float within an outer housing. The electrical connection is preferably made with a flexible wire which would allow the contact housing to slide back and forth with very little friction. Referring to FIG. 12, an embodiment along these lines is shown where a cross section of the housing 600 includes a contact 604 and an active rod 602.

The inside of the contact housing 606 is driven by the sizing requirements of the spring contact 604. The outside of the housing 606 is preferably square or rectangular. The contact housing fits inside of an outer housing 608 with a small clearance. The outer housing 608 is preferably sized to allow the inner housing 606 to move at least as much as the actuation distance of the worst case articulated instrument. The housing preferably has a chamfer on its distal end to guide the rod during insertion.

A flexible wire 610 is connected to both the contact housing 606 and an active wire 612. There are a number of solutions to the type of wire and connection means used. A connection of this type allows the contact housing 606 to slide back and forth in the outer housing with very little friction compared to the current situation of the contact on the rod. The square cross section of the contact housing and the outer housing keeps the wire from being rotated and possibly being bent or hindering the movement between the contact housing 606 and the outer housing 608.

In use, the active rod 602 is inserted from the distal end 614. As the rod 602 goes through the contact 604, the contact housing 606 is pushed to the end of the chamber 616 created by the outer housing 610. If the instrument is inserted in the handle with the jaws apart, this travel is completed when the contact is closed the first time.

Aspects of the present invention provide, among other things, a system and method for easily, quickly, and safely allowing a surgeon or other user to switch between bipolar and monopolar energy delivery during an electrosurgical procedure, the ability to minimize the friction commonly associated with the use of bipolar instruments, and the ability to incorporate an active electrode monitoring system in both bipolar and monopolar electrosurgical modes. Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A electrical switching system for selectively delivering either bipolar or monopolar electrical energy through a surgical instrument, comprising:
    a generator, the generator comprising a first electrical distribution system for delivering monopolar electrical energy, and a second electrical distribution system for delivering bipolar electrical energy;
    a controller coupled to the generator, for selecting based on an electrical condition at a tine of a surgical instrument, which of the first and second electrical distribution systems to activate, the electrical condition indicating a mode of operation of the surgical instrument, the controller comprising:
        a first pair of relays actively coupled to-the first electrical distribution system;
        a second pair of relays actively coupled to-the second electrical distribution system;
        a switch for selecting either the first electrical distribution system or the second electrical distribution system; and
        a keying circuit coupled to the switch for selectively engaging either the first or second electrical distribution systems.

2. The system of claim 1, wherein the keying circuit comprises:
    an isolator for segregating the monopolar electrical energy from the bipolar electrical energy; and
    control logic for determining which of the first and second electrical distribution systems to activate.

3. The system of claim 1, wherein the generator and the controller are distinct units.

4. The system of claim 1, wherein the generator and the controller are within a single unit.

5. The system of claim 1, further comprising a monitoring device coupled to the keying circuit for determining whether a fault condition exists in the surgical instrument.

6. The system of claim 5, wherein the monitoring device is an active electrode monitoring device.

7. The system of claim 5, wherein the monitoring device obtains a voltage reference in order to ascertain a phase comparison.

8. The system of claim 1, wherein the switch is a foot switch.

9. The system of claim 8, wherein the switch is remote from the generator and controller.

10. The system of claim 1, wherein the switch is integrated with the generator.

11. The system of claim 1, wherein the switch is integrated with the controller.

12. The system of claim 1, wherein the switch further comprises a selector for varying the cut and coagulation properties of the electrical energy.

13. The system of claim 1, wherein one of the first and second sets of relays are selected from the group consisting of high voltage reed relays, field effect transistor relays, and solid state relays.

14. An electrical connection system for selectively delivering one of a plurality of electrical energy modes through a surgical instrument, comprising:
    a generator comprising a first electrical distribution system for delivering a electrical energy in a first mode, and a second electrical distribution system for delivering electrical energy in a second mode;
    a controller coupled to the generator, for selecting based on an electrical condition at a tine of a surgical instrument, which of the first and second electrical distribution systems to activate, the electrical condition indicating a mode of operation of the surgical instrument, the controller comprising:
        a first pair of relays electrically coupled to the first electrical distribution system;
        a second pair of relays electrically coupled to the second electrical distribution system;
        a switch for selecting either the first electrical distribution system or the second electrical distribution system;
        a keying circuit coupled to the switch for selectively engaging either the first or second electrical distribution systems based on the mode of operation of the surgical instrument;
        a third set of relays coupled to the first and second set of relays; and
        an impedance sensing circuit coupled to and disposed between the keying circuit and the third set of relays.

15. The system of claim 14, wherein the keying circuit comprises:
    an isolator for segregating the first electrical energy mode from the second electrical energy mode; and
    control logic for determining which of the first and second electrical distribution systems to activate.

16. The system of claim 15, wherein the impedance sensing circuit is coupled to the control logic.

17. The system of claim 14, wherein the generator and the controller are distinct units.

18. The system of claim 14, wherein the generator and the controller are within a single unit.

19. The system of claim 14, further comprising a monitoring device coupled to the keying circuit for determining whether a fault condition exists in the surgical instrument.

20. The system of claim 19, wherein the monitoring device is an active electrode monitoring device.

21. The system of claim 19, wherein the monitoring device obtains a voltage reference in order to ascertain a phase comparison.

22. The system of claim 14, wherein the switch is a foot switch.

23. The system of claim 14, further comprising a second switch for activating or deactivating the flow of electrical energy from the generator to the surgical instrument.

24. The system of claim 14, wherein the switch is remote from the generator and controller.

25. The system of claim 14, wherein the switch is integrated with the generator.

26. The system of claim 14, wherein the switch is integrated with the controller.

27. The system of claim 14, wherein the switch further comprises a selector for varying the cut and coagulation properties of the electrical current.

28. The system of claim 14, wherein one of the first and second sets of relays are selected from the group consisting of high voltage reed relays, field effect transistor relays, and solid state relays.

29. The system of claim 14 wherein the impedance sensing circuit senses a property associated with the surgical instrument and instructs the controller to select either the first or second electrical distribution systems based on the property associated with the electrosurgical instrument.

30. The system of claim 14, wherein the plurality of electrical energy modes comprises bipolar electrical energy and monopolar electrical energy.

31. A method of selectively delivering bipolar or monopolar electrical current through a surgical instrument, comprising:

sensing an electrical condition at a tine of the surgical instrument, the electrical condition indicating a mode of operation of the surgical instrument;

selecting, based on the electrical condition, whether to deliver the bipolar or monopolar electrical current through the surgical instrument; and providing instructions to an electrosurgical generator to deliver the selected bipolar or monopolar electrical current through the surgical instrument.

32. The method of claim 31, wherein the electrical condition is impedance.

* * * * *